US012802809B2

(12) United States Patent
Hooyman

(10) Patent No.: US 12,802,809 B2
(45) Date of Patent: Nov. 17, 2026

(54) METHODS, SYSTEMS, AND COMPUTER READABLE MEDIA FOR GRADING FIGURE DRAWING VISUOSPATIAL TESTS

(71) Applicant: ARIZONA BOARD OF REGENTS ON BEHALF OF ARIZONA STATE UNIVERSITY, Scottsdale, AZ (US)

(72) Inventor: Andrew Hooyman, Las Vegas, NV (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 235 days.

(21) Appl. No.: 18/166,184

(22) Filed: Feb. 8, 2023

(65) Prior Publication Data

US 2023/0260644 A1 Aug. 17, 2023

Related U.S. Application Data

(60) Provisional application No. 63/310,895, filed on Feb. 16, 2022.

(51) Int. Cl.
*G16H 40/63* (2018.01)
*G16H 50/20* (2018.01)

(52) U.S. Cl.
CPC ............ *G16H 40/63* (2018.01); *G16H 50/20* (2018.01)

(58) Field of Classification Search
CPC ........ G16H 40/63; G16H 50/20; G16H 50/70; G16H 30/40; G16H 50/30; G16H 15/00
USPC ........................................................... 705/2
See application file for complete search history.

(56) References Cited

U.S. PATENT DOCUMENTS

| | | | | |
|---|---|---|---|---|
| 2019/0304090 | A1* | 10/2019 | Wang | G06T 7/0012 |
| 2022/0007995 | A1* | 1/2022 | Schuijers | G16H 20/70 |

OTHER PUBLICATIONS

Xiaonan Zhang et al. "Overview of the Complex Figure Test and Its Clinical Application in Neuropsychiatric Disorders, Including Copying and Recall" Front. Neurol., Aug. 30, 2021; Sec. Dementia and Neurodegenerative Diseases, vol. 12—2021 https://doi.org/10.3389/fneur.2021.680474, pp. 1-10.*

(Continued)

*Primary Examiner* — Igor N Borissov

(74) *Attorney, Agent, or Firm* — MH2 Technology Law Group LLP

(57) ABSTRACT

Provided herein are methods of generating neuropsychological functioning scores from test subject data. The methods include receiving a set of images produced by a test subject in which at least a first of the images comprises a rendition of a target image produced by the test subject at a first time point, and in which at least a second of the images comprises a rendition of the target image produced by the test subject at a second time point that differs from the first time point to produce the test subject data. The methods further include passing the test subject data through a trained machine learning algorithm and outputting from the trained machine learning algorithm a neuropsychological functioning score indicated by the test subject data. Additional methods as well as related systems and computer readable media are also provided.

13 Claims, 10 Drawing Sheets

(56) References Cited

OTHER PUBLICATIONS

Kaiming He et al. "Deep Residual Learning for Image Recognition" Computer Vision and Pattern Recognition (cs.CV) arXiv: 1512.03385 [cs.CV] https://doi.org/10.48550/arXiv.1512.03385, 2015, pp. 1-12.*

Andre Esteva et al. "Dermatologist-level classification of skin cancer with deep neural networks".*

* cited by examiner

METHODS, SYSTEMS, AND COMPUTER READABLE MEDIA FOR GRADING FIGURE DRAWING VISUOSPATIAL TESTS

CROSS-REFERENCE TO RELATED APPLICATIONS

This application claims the benefit of U.S. Provisional Application No. 63/310,895 filed Feb. 16, 2022, the disclosure of which is incorporated herein in its entirety.

BACKGROUND

Visuospatial tests such as the Rey-Osterreith Complex Figure Test (ROCFT) involve the drawing of a complex figure that is then graded by a trained neuropsychologist. Recent research has demonstrated that scores on this assessment are linked to motor skill learning as well as well future cognitive status (e.g., Mild Cognitive Impairment diagnosis). With the advent of blood-based biomarkers and telehealth tools (developed both prior to and during the COVID-19 pandemic), collecting and grading the ROOF and other related measures (e.g., clock drawing) remotely and/or at a large scale remain challenging.

Therefore, there is a need for methods, and related aspects, for machine learning applications to provide accurate, fast, and remote scoring of figure drawing tests.

SUMMARY

The present disclosure relates, in certain aspects, to methods of generating a neuropsychological functioning score from test subject data. Some implementations provide a web-based analytical pipeline that automates the scoring of hand-drawn figure tests, such as the ROCFT, among others. These and other aspects will be apparent upon a complete review of the present disclosure, including the accompanying FIGURES.

In one aspect, the present disclosure provides a method of generating a neuropsychological functioning score from test subject data using a computer. The method includes receiving, by the computer, a set of images produced by a test subject in which at least a first of the images comprises a rendition of a target image produced by the test subject at a first time point, and in which at least a second of the images comprises a rendition of the target image produced by the test subject at a second time point that differs from the first time point to produce the test subject data. The method also includes passing, by the computer, the test subject data through a machine learning algorithm in which the machine learning algorithm has been trained on a set of training data that comprises a plurality of reference subject data sets that are each labeled with at least a neuropsychological functioning score of a given reference subject data set in the plurality of reference subject data sets, in which the plurality of reference subject data sets comprises sets of images produced by reference subjects, and in which at least a first and a second of the images in a given set comprises renditions of the target image produced by a given reference subject at different time points. In addition, the method also includes outputting, by the computer, from the machine learning algorithm at least a neuropsychological functioning score indicated by the test subject data, thereby generating the neuropsychological functioning score from the test subject data.

In some embodiments, the set of training data comprises at least about 10 reference subject data sets, at least about 100 reference subject data sets, at least about 1,000 reference subject data sets, at least about 10,000 reference subject data sets, at least about 100,000 reference subject data sets, at least about 1,000,000 reference subject data sets, at least about 10,000,000 reference subject data sets, at least about 100,000,000 reference subject data sets, or more reference subject data sets.

In some embodiments, the method includes, for example, as preprocessing step, vectorizing the set of images produced by the test subject. In some embodiments, the set of images produced by the test subject comprises a Rey Osterrieth Complex Figure Test (ROCFT) assessment. In some embodiments, the neuropsychological functioning score comprises one or more of a visuospatial recall memory score, a visuospatial recognition memory score, a response bias score, a processing speed score, and a visuospatial constructional ability score.

In some embodiments, the method further includes ordering one or more medical tests for, and/or administering one or more therapies to, the test subject when the neuropsychological functioning score indicated by the test subject data varies from a predetermined threshold value. In some embodiments, the method further includes discontinuing administering one or more therapies to the test subject when the neuropsychological functioning score indicated by the test subject data varies from a predetermined threshold value. In some embodiments, the method further includes generating a medical report for the test subject when the neuropsychological functioning score indicated by the test subject data varies from a predetermined threshold value.

In some embodiments, the machine learning algorithm comprises a support vector machine regression (SVMr) algorithm. In some embodiments, the machine learning algorithm comprises an electronic neural network. In some embodiments, the electronic neural network comprises at least one layer that performs a regression operation to generate the neuropsychological functioning score.

In one aspect, the present disclosure provides a system for generating a neuropsychological functioning score from test subject data using a machine learning algorithm. The system includes a processor, and a memory communicatively coupled to the processor, the memory storing instructions which, when executed on the processor, perform operations comprising: passing the test subject data through the machine learning algorithm in which the machine learning algorithm has been trained on a set of training data that comprises a plurality of reference subject data sets that are each labeled with at least a neuropsychological functioning score of a given reference subject data set in the plurality of reference subject data sets, in which the plurality of reference subject data sets comprises sets of images produced by reference subjects, and in which at least a first and a second of the images in a given set comprises renditions of the target image produced by a given reference subject at different time points; and outputting from the machine learning algorithm at least a neuropsychological functioning score indicated by the test subject data.

In one aspect, the present disclosure provides a computer readable media comprising non-transitory computer executable instruction which, when executed by at least electronic processor, perform at least: passing test subject data through a machine learning algorithm, in which the machine learning algorithm has been trained on a set of training data that comprises a plurality of reference subject data sets that are each labeled with at least a neuropsychological functioning score of a given reference subject data set in the plurality of reference subject data sets, in which the plurality of reference subject data sets comprises sets of images produced by reference subjects, and in which at least a first and a second of the images in a given set comprises renditions of the target image produced by a given reference subject at different time points, and outputting from the machine learning algorithm at least a neuropsychological functioning score indicated by the test subject data.

In some embodiments of the systems and computer readable media disclosed herein, the set of training data comprises at least about 10 reference subject data sets, at least about 100 reference subject data sets, at least about 1,000 reference subject data sets, at least about 10,000 reference subject data sets, at least about 100,000 reference subject data sets, at least about 1,000,000 reference subject data sets, at least about 10,000,000 reference subject data sets, at least about 100,000,000 reference subject data sets, or more reference subject data sets. In some embodiments of the systems and computer readable media disclosed herein, the test subject data comprises a vectorization of the set of images produced by the test subject.

In some embodiments of the systems and computer readable media disclosed herein, the test subject data comprises a Rey Osterrieth Complex Figure Test (ROCFT) assessment. In some embodiments of the systems and computer readable media disclosed herein, the neuropsychological functioning score comprises one or more of a visuospatial recall memory score, a visuospatial recognition memory score, a response bias score, a processing speed score, and a visuospatial constructional ability score.

In some embodiments, the system orders one or more medical tests for, and/or recommends administering one or more therapies to, the test subject when the neuropsychological functioning score indicated by the test subject data varies from a predetermined threshold value. In some embodiments, the system recommends discontinuing administering one or more therapies to the test subject when the neuropsychological functioning score indicated by the test subject data varies from a predetermined threshold value. In some embodiments, the system generates a medical report for the test subject when the neuropsychological functioning score indicated by the test subject data varies from a predetermined threshold value.

In some embodiments of the systems and computer readable media disclosed herein, the machine learning algorithm comprises a support vector machine regression (SVMr) algorithm. In some embodiments of the systems and computer readable media disclosed herein, the machine learning algorithm comprises an electronic neural network. In some embodiments of the systems and computer readable media disclosed herein, the electronic neural network comprises at least one layer that performs a regression operation to generate the medical concordance score.

In one aspect, the present disclosure provides a method of predicting a motor skill performance score from test subject data using a computer. The method includes receiving, by the computer, at least one rendition of a target image produced by a test subject to produce the test subject data. The method also includes passing, by the computer, the test subject data through a machine learning algorithm, in which the machine learning algorithm has been trained on a set of training data that comprises a plurality of reference subject data sets that are each labeled with at least a motor skill performance score of a given reference subject data set in the plurality of reference subject data sets, and in which the plurality of reference subject data sets comprises renditions of the target image produced by reference subjects. In addition, the method also includes outputting, by the computer, from the machine learning algorithm at least a motor skill performance score indicated by the test subject data.

In one aspect, the present disclosure provides a system for predicting a motor skill performance score from test subject data using a machine learning algorithm. The system includes a processor, and a memory communicatively coupled to the processor, the memory storing instructions which, when executed on the processor, perform operations comprising: passing the test subject data through a machine learning algorithm, in which the test subject data comprises at least one rendition of a target image produced by a test subject, in which the machine learning algorithm has been trained on a set of training data that comprises a plurality of reference subject data sets that are each labeled with at least a motor skill performance score of a given reference subject data set in the plurality of reference subject data sets, and in which the plurality of reference subject data sets comprises renditions of the target image produced by reference subjects; and outputting from the machine learning algorithm at least a motor skill performance score indicated by the test subject data.

In one aspect, the present disclosure provides a computer readable media comprising non-transitory computer executable instruction which, when executed by at least electronic processor, perform at least: passing test subject data through a machine learning algorithm, in which the test subject data comprises at least one rendition of a target image produced by a test subject, in which the machine learning algorithm has been trained on a set of training data that comprises a plurality of reference subject data sets that are each labeled with at least a motor skill performance score of a given reference subject data set in the plurality of reference subject data sets, and which the plurality of reference subject data sets comprises renditions of the target image produced by reference subjects; and outputting from the machine learning algorithm at least a motor skill performance score indicated by the test subject data.

BRIEF DESCRIPTION OF THE DRAWINGS

The accompanying drawings, which are incorporated in and constitute a part of this specification, illustrate certain embodiments, and together with the written description, serve to explain certain principles of the methods, systems, and related computer readable media disclosed herein. The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the FIGURES may be schematic representations for purposes of illustration and do not necessarily depict the actual relative sizes or locations of the elements shown.

DEFINITIONS

Figure 1:
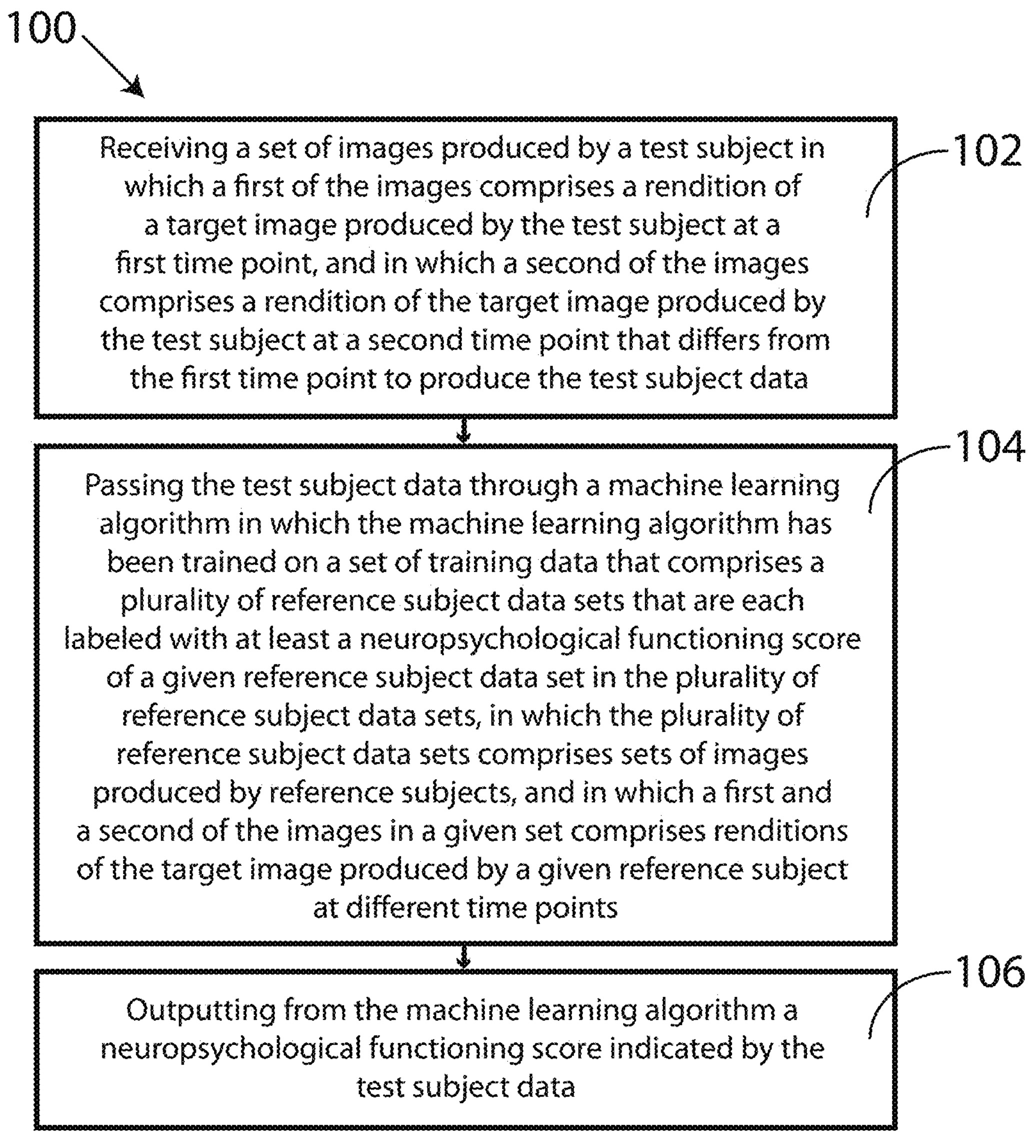
FIG. 1 is a flow chart that schematically shows exemplary method steps of generating a neuropsychological functioning score from test subject data according to some aspects disclosed herein.

In order for the present disclosure to be more readily understood, certain terms are first defined below. Additional definitions for the following terms and other terms may be set forth throughout the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

It is also to be understood that the terminology used herein is for the purpose of describing particular embodiments only and is not intended to be limiting. Further, unless defined otherwise, all technical and scientific terms used herein have the same meaning as commonly understood by one of ordinary skill in the art to which this disclosure pertains. In describing and claiming the methods, systems, and computer readable media, the following terminology, and grammatical variants thereof, will be used in accordance with the definitions set forth below.

About: As used herein, "about" or "approximately" or "substantially" as applied to one or more values or elements of interest, refers to a value or element that is similar to a stated reference value or element. In certain embodiments, the term "about" or "approximately" or "substantially" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Classifier: As used herein, "classifier" generally refers to algorithm computer code that receives, as input, test data and produces, as output, a classification of the input data as belonging to one or another class.

Data set: As used herein, "data set" refers to a group or collection of information, values, or data points related to or associated with one or more objects, records, and/or variables. In some embodiments, a given data set is organized as, or included as part of, a matrix or tabular data structure. In some embodiments, a data set is encoded as a feature vector corresponding to a given object, record, and/or variable, such as a given test or reference subject. For example, a medical data set for a given subject can include one or more observed values of one or more variables associated with that subject.

Electronic neural network: As used herein, "electronic neural network" refers to a machine learning algorithm or model that includes layers of at least partially interconnected artificial neurons (e.g., perceptrons or nodes) organized as input and output layers with one or more intervening hidden layers that together form a network that is or can be trained to classify data, such as test subject medical data sets (e.g., medical images or the like).

Labeled: As used herein, "labeled" in the context of data sets or points refers to data that is classified as, or otherwise associated with, having or lacking a given characteristic or property.

Machine Learning Algorithm: As used herein, "machine learning algorithm" generally refers to an algorithm, executed by computer, that automates analytical model building, e.g., for clustering, classification or pattern recognition. Machine learning algorithms may be supervised or unsupervised. Learning algorithms include, for example, artificial neural networks (e.g., back propagation networks), discriminant analyses (e.g., Bayesian classifier or Fischer analysis), support vector machines, decision trees (e.g., recursive partitioning processes such as CART-classification and regression trees, or random forests), linear classifiers (e.g., multiple linear regression (MLR), partial least squares (PLS) regression, and principal components regression), hierarchical clustering, and cluster analysis. A dataset on which a machine learning algorithm learns can be referred to as "training data."

Subject: As used herein, "subject" or "test subject" refers to an animal, such as a mammalian species (e.g., human) or avian (e.g., bird) species. More specifically, a subject can be a vertebrate, e.g., a mammal such as a mouse, a primate, a simian or a human. Animals include farm animals (e.g., production cattle, dairy cattle, poultry, horses, pigs, and the like), sport animals, and companion animals (e.g., pets or support animals). A subject can be a healthy individual, an individual that has or is suspected of having a disease or pathology or a predisposition to the disease or pathology, or an individual that is in need of therapy or suspected of needing therapy. The terms "individual" or "patient" are intended to be interchangeable with "subject." A "reference subject" refers to a subject known to have or lack specific properties (e.g., a known pathology, such as melanoma and/or the like).

System: As used herein, "system" in the context of medical or scientific instrumentation refers a group of objects and/or devices that form a network for performing a desired objective.

Threshold: As used herein, "threshold" refers to a separately determined value used to characterize or classify experimentally determined values.

Value: As used herein, "value" generally refers to an entry in a dataset that can be anything that characterizes the feature to which the value refers. This includes, without limitation, numbers, words or phrases, symbols (e.g., + or −) or degrees.

DETAILED DESCRIPTION

Within neuropsychology there is an assessment called the ROCFT, where a clinician will have a patient complete 3 drawings of a complex figure. Typically, the clinician then grades the drawings by hand using a specific grading criteria. Some aspects disclosed herein disclose an algorithm that can take digital pictures of these drawings and complete the grading without any human assistance. This allows for grading of the FIGURES to be completed automatically and at high speed and with good reliability saving the clinician time on grading. Currently, there are no clinical tools in practice or within the scientific field capable of this. An exemplary purpose of this disclosure is to give time back to clinicians by automating grading of an important clinical assessment, the ROCFT. Importantly, the algorithm can be implemented within a web-based application so all that needs to be done for the algorithm to work is having the patient drawings scanned into a digital copy. Once in this digital form, the images can be uploaded to the application and graded within a matter of seconds.

More specifically, the present disclosure pertains, in some aspects, to the field of neuropsychology. For example, it is of interest for assessment among older aged patients who may be experiencing cognitive decline. One aspect of assessing a patient's cognition is based upon their visuospatial memory, which is the process of copying and/or recalling an image. Assessment of this visual memory is typically done using the Rey Osterrieth Complex Figure Test (ROCFT). The ROCFT uses a specific complex figure, i.e. an image with what appears to be random geometric shapes and designs, which a patient must first copy and recall, i.e. a patient attempts to draw the complex figure as precisely as possible with and without the original complex figure as an aid. Once the patient completes the drawings a trained clinician then grades them based on a specific rubric. The resulting grade of each image provides the clinician with specific information about a patient's visual memory. This information has found to be important for diagnosis and prognosis of a patient's long term cognitive trajectory. However, complete grading of the ROCFT can take up to 20 to 30 minutes. This time constraint makes actual use of the ROCFT not as wide-spread as many clinicians would like. With the future aging of the US population indeed the ROCFT will need to be used more and not less in clinical practice. Thus, an exemplary aim of the present disclosure is to provide clinicians with a clinical tool designed to automatically grade the ROCFT so the time needed to grade can be given back to clinicians without cost of grading accuracy.

In some aspects, the Rey Osterrieth Complex Figure Test (ROCFT) automated grading tool takes digital images of the ROCFT and returns human accurate grades 400× faster than average human performance. Thus, the ROCFT automated grading tool gives time back to the clinician. In some aspects, the ROCFT is an important clinical tool in the field of neuropsychology and aging for evaluating visual memory of older adults with and without dementia, but can often be underutilized due to the time needed to accurately grade, especially since grading can only be performed by a trained professional. This makes it difficult for clinicians to "off-load" the grading process to a subordinate which would still take time and money to be completed. The ROCFT automated grading tool is available on any internet connected device as it has been implemented as an online web app. In some embodiments, a clinician only needs a digital scan of the ROCFT complex FIGURES, upload them to the app and within seconds receive grades on all assessments. In some implementations, the ROCFT automated grading tool disclosed herein can grade 100 complex FIGURES in less than two seconds. Typically, for a clinician to complete the grading of 3 complex FIGURES for one patient it can take anywhere from 20 to 30 minutes.

Exemplary Methods

In some aspects, the present disclosure provides a method of generating a neuropsychological functioning score from test subject data using a computer. As shown in FIG. 1, for example, method 100 includes receiving a set of images produced by a test subject in which at least a first of the images comprises a rendition of a target image produced by the test subject at a first time point, and in which at least a second of the images comprises a rendition of the target image produced by the test subject at a second time point that differs from the first time point to produce the test subject data (step 102). Method 100 also includes passing the test subject data through a machine learning algorithm in which the machine learning algorithm has been trained on a set of training data that comprises a plurality of reference subject data sets that are each labeled with at least a neuropsychological functioning score of a given reference subject data set in the plurality of reference subject data sets, in which the plurality of reference subject data sets comprises sets of images produced by reference subjects, and in which at least a first and a second of the images in a given set comprises renditions of the target image produced by a given reference subject at different time points (step 104). In addition, method 100 also includes outputting from the machine learning algorithm at least a neuropsychological functioning score indicated by the test subject data, thereby generating the neuropsychological functioning score from the test subject data (step 106).

In some embodiments, the set of training data comprises at least about 10 reference subject data sets, at least about 100 reference subject data sets, at least about 1,000 reference subject data sets, at least about 10,000 reference subject data sets, at least about 100,000 reference subject data sets, at least about 1,000,000 reference subject data sets, at least about 10,000,000 reference subject data sets, at least about 100,000,000 reference subject data sets, or more reference subject data sets.

In some embodiments, the method includes, for example, as preprocessing step, vectorizing the set of images produced by the test subject. In some embodiments, the set of images produced by the test subject comprises a Rey Osterrieth Complex Figure Test (ROCFT) assessment. In some embodiments, the neuropsychological functioning score comprises one or more of a visuospatial recall memory score, a visuospatial recognition memory score, a response bias score, a processing speed score, and a visuospatial constructional ability score.

In some embodiments, the method further includes ordering one or more medical tests for, and/or administering one or more therapies to, the test subject when the neuropsychological functioning score indicated by the test subject data varies from a predetermined threshold value. In some embodiments, the method further includes discontinuing administering one or more therapies to the test subject when the neuropsychological functioning score indicated by the test subject data varies from a predetermined threshold value. In some embodiments, the method further includes generating a medical report for the test subject when the neuropsychological functioning score indicated by the test subject data varies from a predetermined threshold value.

In some embodiments, the machine learning algorithm comprises a support vector machine regression (SVMr) algorithm. In some embodiments, the machine learning algorithm comprises an electronic neural network. In some embodiments, the electronic neural network comprises at least one layer that performs a regression operation to generate the neuropsychological functioning score.

Preprocessing Steps for Conversion of Uploaded Pdf Documents to Algorithm Readable Data Vectors In some embodiments, after a user has uploaded a pdf document it is first converted into a grayscale "magick-image" using the magick library available in R. Use of the magick library allows for image processing within the R IDE. The image is then scaled to width of 90 pixels and a height of 124 pixels, with a total of 11,160 pixels total using the image_scale function. At this level each pixel contains three hex values representing its grayscale value. Grayscale hex values are simply triplets of a single hex value, for example FFFFFF is the color white and 000000 is the color black. The raw pixel data at this step for the bitmap is a 90×124×4 matrix. The fourth value in the third dimension of the matrix is the alpha channel which can be ignored for our purposes. I then extract only the first matrix of the scaled bitmap yielding a raw bitmap of 90×124×1. This bitmap is then converted into a workable data frame which I then convert from wide format to long format where the resulting matrix is 11, 60×3, where the first column represents the row of the pixel in the image, the second column represents the column of the pixel in the image and the third column represents the first hex value of the pixel at that row and column in the image. An "ifelse" statement is used to convert each pixel to either a 1 or 0. If a pixel has a value of either "ff", "fe", "fd", "fc", "fb", or "fa" then it is converted to 0 otherwise it is converted to 1. This converted value column is then stored in a new data frame where the 0, 1 values of the converted hex pixels are stored as independent variables to be later inputted in the support vector algorithm that will then provide a predicted image score.

Exemplary Systems and Computer Readable Media

Figure 2:
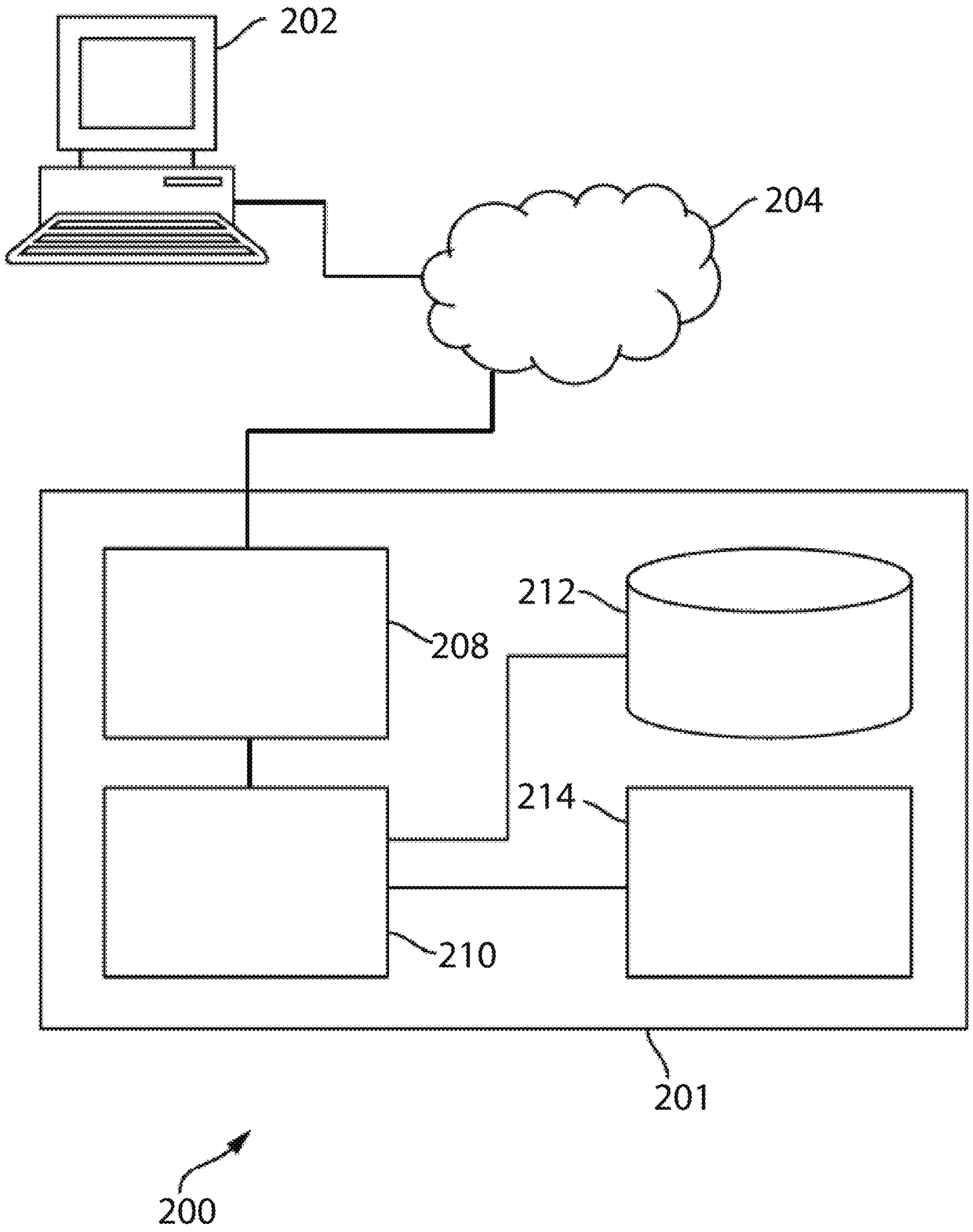
FIG. 2 is a schematic diagram of an exemplary system suitable for use with some aspects disclosed herein.

FIG. 2 is a schematic diagram of a hardware computer system 200 suitable for implementing various embodiments. For example, FIG. 2 illustrates various hardware, software, and other resources that can be used in implementations of any of methods disclosed herein, including method 100 and/or one or more instances of an electronic neural network. System 200 includes training corpus source 202 and computer 201. Training corpus source 202 and computer 201 may be communicatively coupled by way of one or more networks 204, e.g., the Internet. Training corpus source 202 may include an electronic clinical records system, such as an LIS, a database, a compendium of clinical data, or any other source test and/or reference subject data.

Computer 201 may be implemented as any of a desktop computer, a laptop computer, can be incorporated in one or more servers, clusters, or other computers or hardware resources, or can be implemented using cloud-based resources. Computer 201 includes volatile memory 214 and persistent memory 212, the latter of which can store computer-readable instructions, that, when executed by electronic processor 210, configure computer 201 to perform any of the methods disclosed herein, including method 100, and/or form or store any electronic neural network, and/or perform any classification technique as described herein. Computer 201 further includes network interface 208, which communicatively couples computer 201 to training corpus source 202 via network 204. Other configurations of system 200, associated network connections, and other hardware, software, and service resources are possible.

Certain embodiments can be performed using a computer program or set of programs. The computer programs can exist hi a variety of forms both active and inactive. For example, the computer programs can exist as software program(s) comprised of program instructions in source code, object code, executable code or other formats; firmware program(s), or hardware description language (HDL) files. Any of the above can be embodied on a transitory or non-transitory computer readable medium, which include storage devices and signals, in compressed or uncompressed form. Exemplary computer readable storage devices include conventional computer system RAM (random access memory), ROM (read-only memory), EPROM (erasable, programmable ROM), EEPROM (electrically erasable, programmable ROM), and magnetic or optical disks or tapes.

In some aspects, the present disclosure provides a computer readable media comprising non-transitory computer executable instruction which, when executed by at least electronic processor, perform at least: passing test subject data through a machine learning algorithm, in which the machine learning algorithm has been trained on a set of training data that comprises a plurality of reference subject data sets that are each labeled with at least a neuropsychological functioning score of a given reference subject data set in the plurality of reference subject data sets, in which the plurality of reference subject data sets comprises sets of images produced by reference subjects, and in which at least a first and a second of the images in a given set comprises renditions of the target image produced by a given reference subject at different time points, and outputting from the machine learning algorithm at least a neuropsychological functioning score indicated by the test subject data.

EXAMPLES

Example 1: Application of Machine Learning for Grading Figure-Drawing Visuospatial Tests Within neuropsychology it is important to assess a patient's visual spatial function and memory for a complete cognitive profile. Especially as recent research has demonstrated that visual spatial function and memory have been identified as some of the earliest indicators of Mild cognitive impairment and dementia risk. Therefore, tests such as the Rey-Osterrieth Complex Figure Test (ROCFT) are important tools to utilize within clinical practice to assess for cognitive impairment. However, the grading of these tests can be time-consuming and inter-rater reliability can be variable.

Recent advancements in computational power in machine learning algorithms now allows for the accurate and fast prediction of images. Therefore, there is the potential to utile eyes these same machine learning techniques for the fast and accurate grading of the ROCFT. Previous research that has examined the application of computer-based methods to grade complex FIGURES is constrained to specific technological and software requirements. Ideally, an effective grading apparatus would still rely upon paper and pencil administration of the ROCFT which could then be scanned into an online grading application which would instantly provide an accurate grade regardless of whether the test was the Copy, Immediate, or Delayed Recall version of the test. This would allow for the physical test to be stored within the patient's medical record while allowing for grading to occur in any place with an internet connection. Thus, the purpose of this research is to address a need voiced among neuropsychologists to create a simple and web-based application for grading the ROCFT.

The primary aim of this study is to demonstrate the reliability of a machine learning algorithm trained and tested to grade the ROCFT and all of its versions. A secondary aim is to then implement the algorithm onto an online server that will then be used within a web application which we would then test for time to grade single and multiple files. Therefore, the goals of this research are twofold, first, to demonstrate the accuracy of the grading algorithm, and second, to demonstrate the grading speed of the web application.

Methods

To construct this application, we compiled a dataset of 134 ROCFT drawings from cognitively intact older adults in the general community (N=45, mean age: 65.5 y; 29 F) that were graded manually per the test instructions and verified by a clinical neuropsychologist. Participant recruitment and experimental procedures were approved by Arizona State University's Institutional Review Board.

ROCFT images were rescaled (90×124) at 300 ppi, converted from pdf to bitmap formats, and each pixel converted to a 1 or 0 dependent on grayscale value.

All statistical analyses were performed in R (4.0.0). Support Vector Machine regression (SVMr) was used to predict ROCFT scores. The mlr package was used to tune the SVMr, the e1071 package was used to calculate training and test set predictions. Tuned SVMr algorithm was trained on 107 images and tested on 27 images.

Mean absolute error (MAE) was used as our error metric on test set prediction. Intra class correlation of a two-way random effects model was used to determine level of test set accuracy.

TABLE 1

Tuned SVMr Hyperparameters

| Kernal | Epsilon | Gamma | Degree | Cost |
|---|---|---|---|---|
| Linear | 1.85 | 8.66 | 2 | 3.4 |

ROCFT Total Score

This complex figure drawing test comprises two separate trials: A Figure Copy (measures visuospatial construction) and a Delayed Recall (measures delayed visuospatial memory) trial. The tests were administered and manually graded according to test instructions and verified by a clinical neuropsychologist. Briefly, participants were first asked to draw a replicate of a complex image as precisely as possible; once finished, all visual stimuli were removed from the testing area. Thirty minutes later, participants were asked to redraw the figure from memory; this was the Delayed Recall trial (see FIG. 1A). The test is scored such that the more accurate the drawing is to the original image, the more points scored (36 total possible points); thus, higher total scores indicate better delayed visuospatial memory.

Image Processing of Pixel Data

Figure 3:
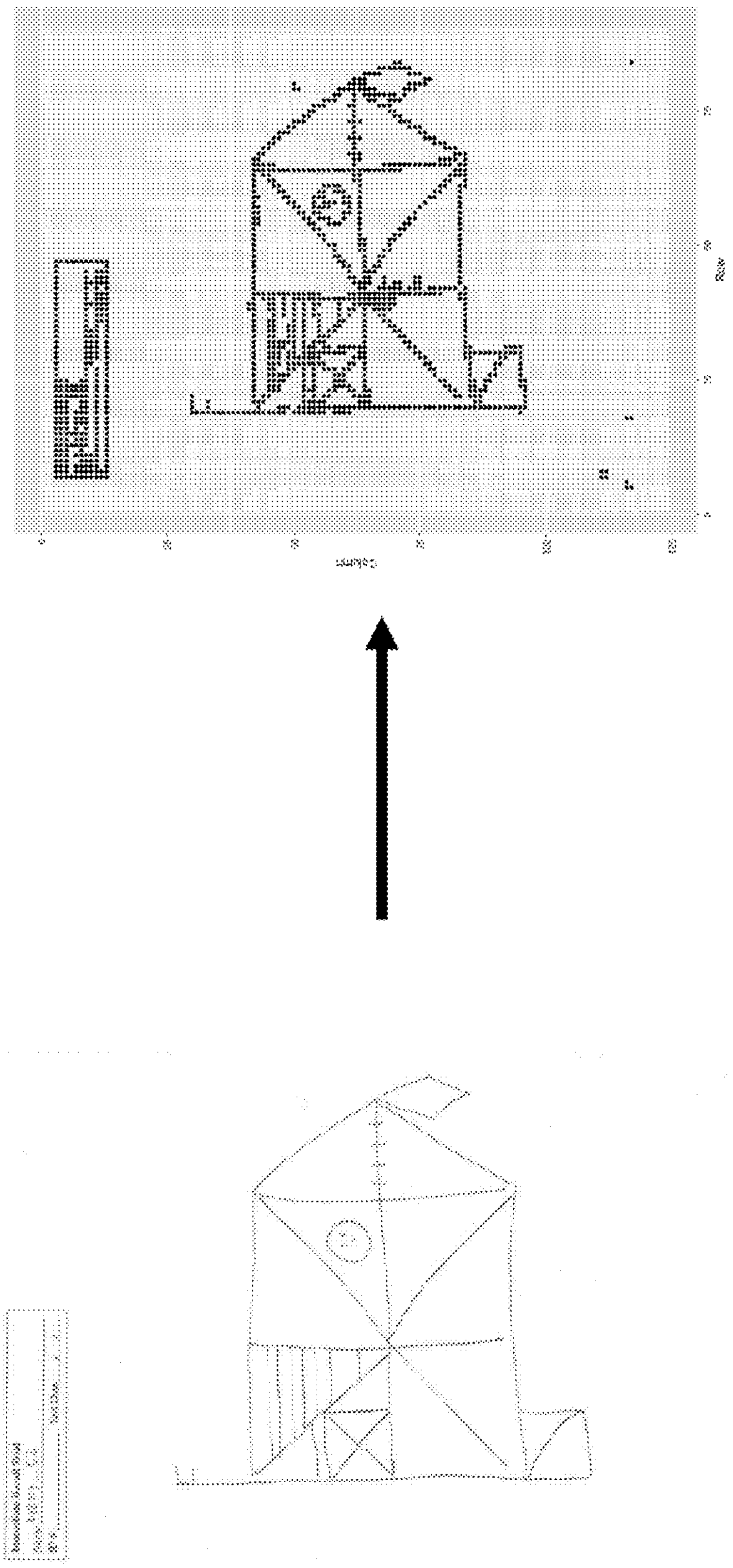
FIG. 3 shows an example of Rey-Osterrieth Complex Test (ROCFT) conversion from portable document format (pdf) to final data format in which each pixel is used as a variable to predict ROCFT scores according to some aspects disclosed herein.
Figure 4A:
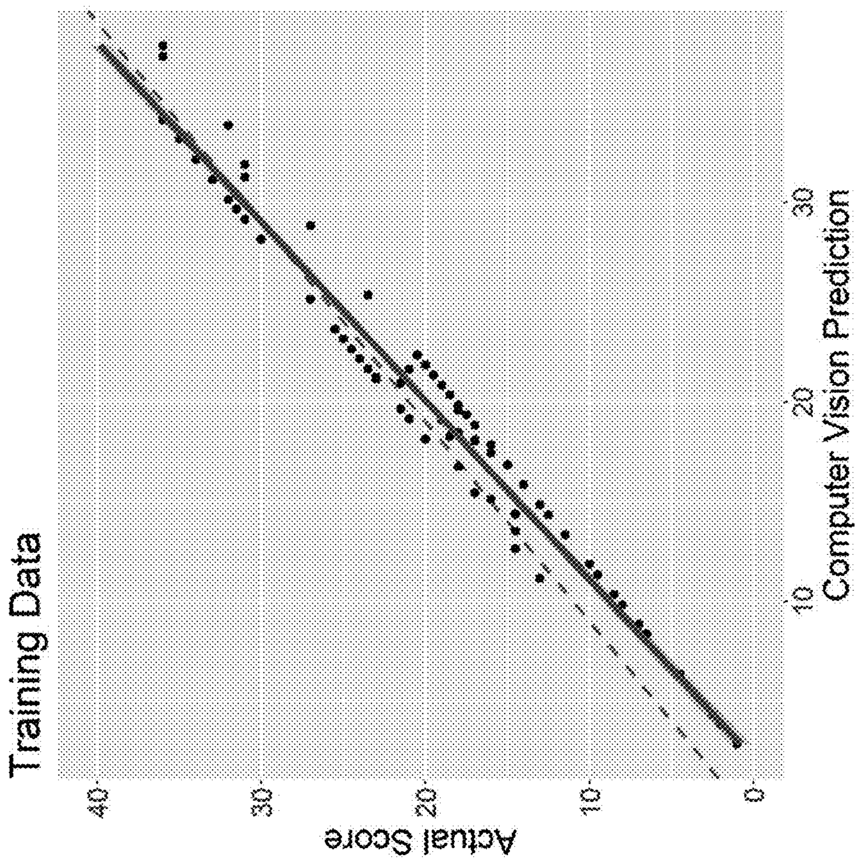
FIGS. 4A-4D show (A) Fitted scores versus actual scores on a training data set; (B) Predicted scores versus actual scores on test set data in which the black dashed line represents perfect prediction 1:1 ratio; (C) Example of converted ROCFT; and (D) Visualization of mapping of average support vector in pixel space.
Figure 4B:
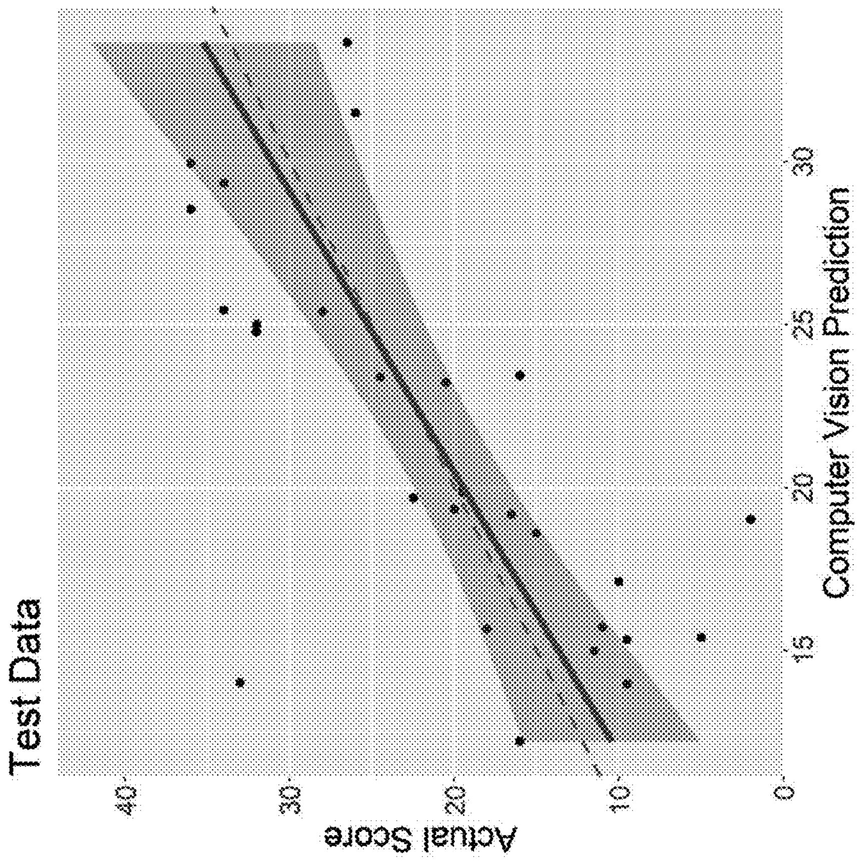
Figure 4D:
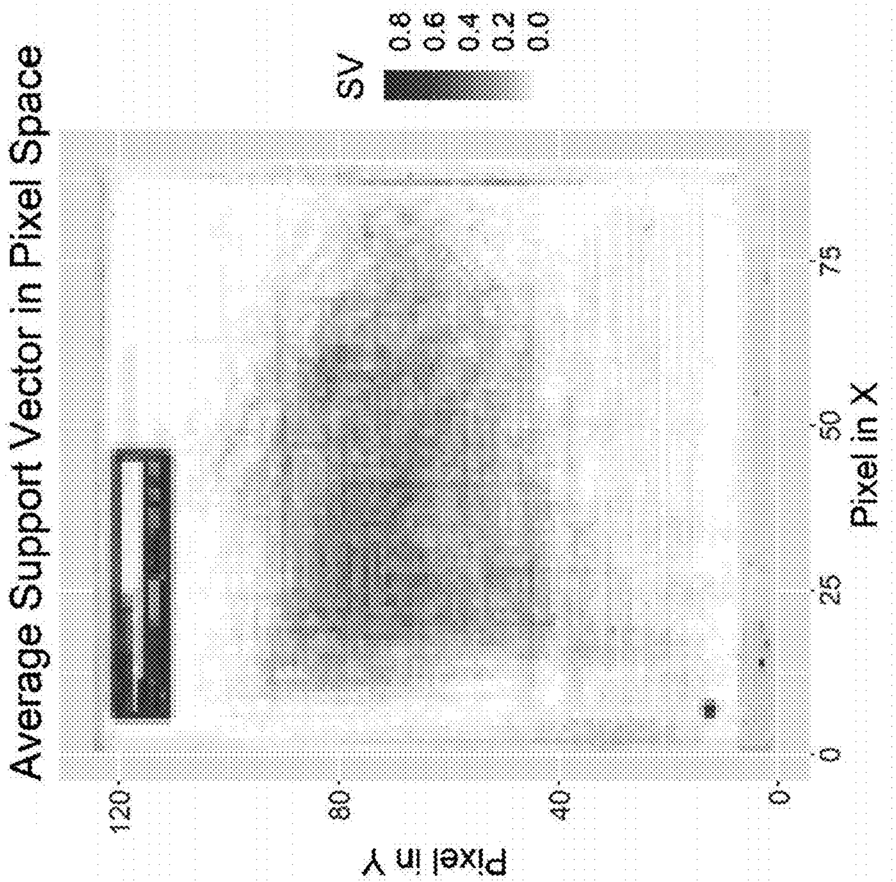
Figure 4C:
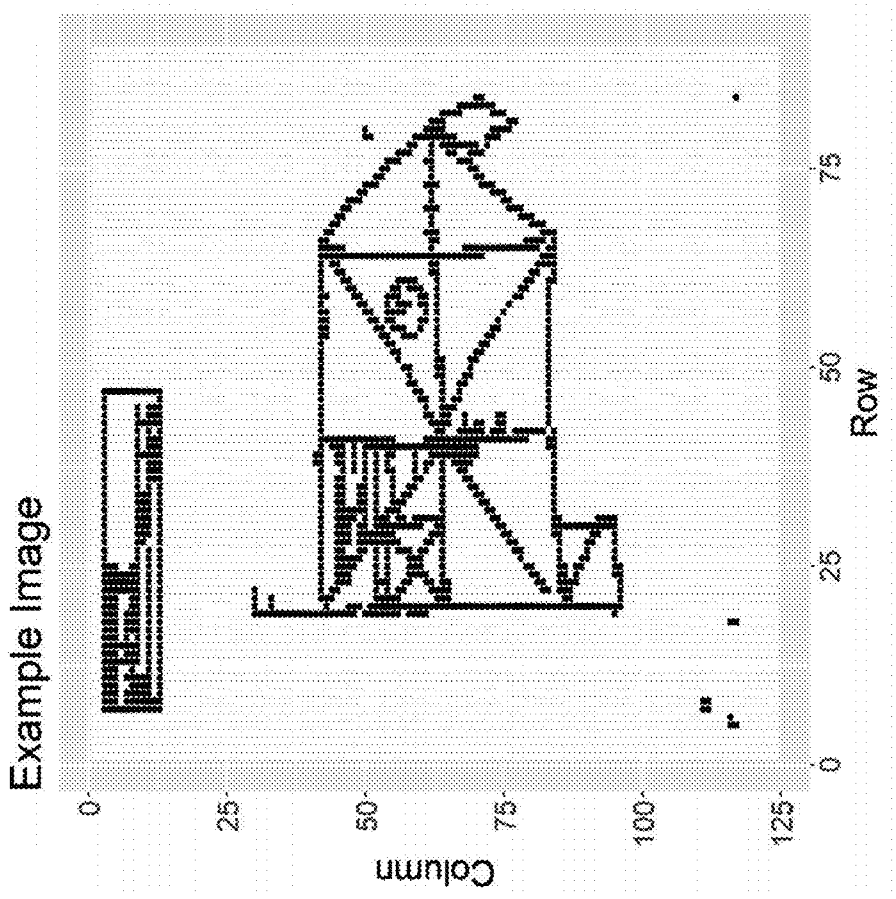

The Delayed Recall drawings were scanned electronically and stored as individual pdf documents. Using the magick package each document was then converted into grayscale and rescaled into a bitmap (90×124 pixels). Each pixel within an image was either converted to black or white depending on if it was of an intensity threshold greater or lesser than 50%, i.e. any pixel that was below this threshold was converted to white. Example of a converted image can be viewed in FIG. 3. Black pixels were then coded as 1 and white pixels were coded as 0 and then each image bitmap was vectorized into a observation by pixel data frame. Respective grades for each image were then concatenated onto the pixel data frame to then be passed into the grading algorithm.

Construction and Tuning of Grading Algorithm

To determine how to produce the most precise grade for each image we trained and tested three machine learning algorithms to examine accuracy. The three algorithms used were neural network (kerns package), support vector machine (e1071 package), and random forest (randomForest package). The support vector machine and random forest were each tuned using the mlr package.

Each algorithm is considered a supervised algorithm, meaning these use the grade of each image and the pixel data to better shape its prediction. To prevent overfitting of the algorithm to the data we performed a 80/20 split, where the data is trained on 80% (N=107) of the data using the image grade and the pixel data to predict, and then tested on 20% (N=27) of the data where the algorithm only uses the pixel data and not the grade to make a prediction. The test set is similar to what the algorithm would experience within a clinical context where it is given an image and it has to make a prediction with only the information it can find within that image. To prevent any bias between training and test sets we partitioned the data so they are similar in score mean and distribution.

The accuracy of each image was determined by calculating the intraclass correlation and mean absolute error between the observed and predicted values of the test set. The intraclass correlation coefficient was used a two-way random-effects model. The algorithm that demonstrated the best overall prediction was then implemented into the web-application to then be further tested for speed of prediction.

Creating of Web-Application and Test of Grading Speed

The web application was then implemented using shinyapps.io, a common web hosting service for applications coded in R. The application was designed so a user can upload either individual or several images at a time. If an individual file was uploaded for grading then the processed imaged would be displayed on the screen and then the user would then click on the grade button to have the predicted score displayed. If several images were uploaded the processed images are not displayed, this is to save on time and computational memory, and when the grade button is clicked a csv file is available for download that has each files name linked with its respective predicted score. To test for how quickly the algorithm processes the uploaded files and then generates a prediction we measured the time taken to complete prediction on 1, 10, 50 and 100 images. This was primarily done to assess if time taken to complete a job of varying size increases either linearly or exponentially and to set expectation of how real-world performance of this algorithm would fair in a real-world implementation. It should be noted that speed of performance is based on the shinyapp servers and not to the researchers machine, thus clinical accessibility to computing power is not rate limiting. Additionally, applications implemented in shiny app are also mobile compatible so use of this application can be done outside the clinic. To quantify how much additional time it takes with the addition of files to be graded we fit a simple linear model to the resulting data.

Results

Grading Algorithm Reliability

The support vector machine algorithm had the best overall prediction accuracy compared to the other two algorithms examined. The detailed results of the training and tuning process can be viewed in the supplementary material. Overall, the support vector machine algorithm achieved a mean absolute error of 5.1 resembling an average prediction error of 5 points from the actual grade. The calculated intraclass correlation was 0.8 ($p<0.001$, 95% CI=[0.61, 0.9], representing good agreement between the human graded score and the algorithm graded score. The accuracy of prediction between observed and predicted outcomes can be viewed in FIG. X. A fitted linear model between the observed and predicted scores was statistically significant ($p<0.001$. $R2=0.51$) with an intercept of 10.51 ($p<0.001$, 95% CI=[6.2, 14.8]) and slope of 0.46 ($p<0.001$, 95% CI=[0.29, 0.65]). If we had achieved perfect prediction on the test set the intercept would be 0 and the slope would be 1. Importantly, the test-retest reliability of the algorithm is 100%, meaning that if the same image is tested on by the image it will always produce the same grade, i.e. the algorithm maintains perfect memory of its training.

Further analysis examined if accuracy of prediction was dependent on score, i.e. does the algorithm have better prediction for lower or higher scores. We determined that the algorithm performs better for higher scores but not as well for lower scores, specifically scores below 15. This is primarily due to the dataset used here has more scores at the higher end than the lower end and thus the algorithm is better trained to predict higher scores.

FIGS. 4A-4D show (A) Fitted scores versus actual scores on a training data set; (B) Predicted scores versus actual scores on test set data in which the black dashed line represents perfect prediction 1:1 ratio; (C) Example of converted ROCFT; and (D) Visualization of mapping of average support vector in pixel space.

Grading Algorithm Speed

Results from assessment of the web-application grading speed demonstrated that a single file takes 2.8 seconds to be processed and graded. Based on our fitted linear model the grading of additional files increases time of grading in a linear fashion. Specifically, it takes on average 1.01 seconds of additional time for every individual file uploaded for grading. For example, the grading of 10 files would take 11.78 seconds and the grading of 100 files would take 152 seconds. We determined that the primary driver of increased testing time is due to the image processing as algorithm grading appears to be constant regardless of number of files included.

Discussion

The purpose of this study was to demonstrate that a trained machine learning algorithm can address the fundamental bottlenecks that limit ease of use of the ROCFT, i.e. accurate human grading that is time consuming. Results demonstrated that a trained algorithm could achieve good agreement with a human rater and can do so at high speed—potentially 100× faster than a human grader. Overall, the formulation and implementation of this ROCFT grading algorithm demonstrates the unique capability of machine learning to streamline the capability to use assessments that utilize a complex figure.

Importantly, the image processing utilized as part of the ROCFT grading pipeline was developed as if the administration of the ROCFT were to remain unchanged, i.e. continued to be completed by a patient via paper and pencil. Other research have tried to have cognitive tests administered on a digital device and have found that performance differences can occur to whether a person completes the assessment on a digital device versus a pen and paper test. Additionally, individual ROCFT FIGURES varied in size and position yet the algorithm was still robust to these between figure discrepancies meaning that image segmentation or editing is not needed for accurate score prediction. This varies from other methods that use digital grading of a complex figure that may remove information within the exam that may be informative for grading.

Another aim of this research is to not only give back time to clinicians but to also increase the usage of the ROCFT in clinical and research contexts. Changes in ROCFT performance overtime has been found to be one of the earliest indicators of cognitive decline related to dementia. Therefore, ease with which the ROCFT can be used can boost important patient information for clinical practice and the implementation of this algorithm can help contribute to that goal without modification to current practice.

Example 2: Using Image Processing to Compare Linear and Machine Learning Models of One-Month Upper-Extremity Motor Skill Performance in Older Adults Introduction Successful clinical motor rehabilitation outcomes largely depend upon an individual's ability to learn novel motor skills. However, responsiveness to rehabilitation is difficult to predict due in part to individual differences in the structural; functional integrity of neural networks underlying motor skill learning. The ability to predict the extent of motor learning could help therapists streamline and personalize patient treatments, and has been the recent focus of a number of studies. Unfortunately, most predictive tools or models are time-intensive and/or expensive (e.g., annual clinical measures, neuroimaging, etc.).

In contrast, there is mounting evidence suggesting that upper-extremity motor skill learning and visuospatial processes are positively linked, such that visuospatial function may be an overlooked clinical predictor of motor therapy responsiveness. We recently reported that the Rey-Osterrieth Complex Figure Delayed Recall Test (a measure of delayed visuospatial memory) predicted one-month upper-extremity motor skill retention in nondemented older adults, and that the inclusion of Delayed Recall scores improved prediction accuracy of skill retention in non-disabled older adults and individuals with stroke.

Three nontrivial limitations to using the Delayed Recall test (and other figure drawing tests) in clinical and experimental settings, however, are that it 1) uses manual scoring by a trained neuropsychologist, 2) is susceptible to high interrater variability, and 3) is difficult to collect and grade remotely. To address these issues, we used machine learning algorithms capable of handling pixel data to develop an analytical pipeline that automates the scoring of hand-drawn figure tests such as the Delayed Recall test. To date, the feasibility of this algorithm in research-based applications remains unexplored. Thus, the purpose of this example was to evaluate the utility of the automated scoring algorithm in research-based applications, and to compare the prediction accuracy of this model with our model using manually scored images to predict one-month motor skill performance. We hypothesized that the machine learning model would demonstrate comparable performance as that of a model that used manually scored Delayed Recall tests to predict one-month follow-up performance on an upper-extremity motor task.

Method

Participant recruitment and experimental procedures were approved by Arizona State University's Institutional Review Board. Forty-three nondemented older adults (mean age: 65.5 years; 29 F) previously completed the visuospatial testing (Delayed Recall) and motor training paradigm; results indicated that Delayed Recall total test scores (measures delayed visuospatial memory) predicted one-month follow-up performance of an upper-extremity motor task. The example described here evaluated whether an automated grading algorithm can be used to replicate those findings. Specifically, the objective of these secondary analyses was to compare the prediction accuracy of one-month motor task performance of various machine learning approaches that used pixel data from the image (pixelated Delayed Recall image) compared to a linear model that used the Delayed Recall total score.

A. Delayed Recall Total Score

This complex figure drawing test comprises two separate trials; A Figure Copy (measures visuospatial construction) and a Delayed Recall (measures delayed visuospatial memory) trial. The tests were administered and manually graded according to test instructions and verified by a clinical neuropsychologist. Briefly, participants were first asked to draw a replicate of a complex image as precisely as possible; once finished, all visual stimuli were removed from the testing area. Thirty minutes later, participants were asked to redraw the figure from memory; this was the Delayed Recall trial (see Fla 5A). The test is scored such that the more accurate the drawing is to the original image, the more points scored (36 total possible points); thus, higher total scores indicate better delayed visuospatial memory. Based on previous work, out of 6 standardized visuospatial tests, Delayed Recall total score was the most accurate predictor of long-term retention on a complex motor task and was therefore chosen for our analysis.

B. Delayed Recall Pixel Data

Figure 5C:
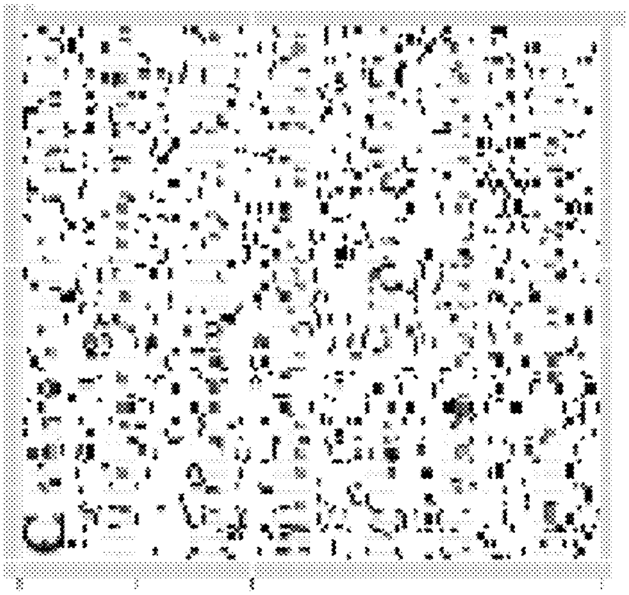
FIGS. 5A-5C show exemplary recall drawings for (A) total score, (B) pixel data, and (C) scrambled.
Figure 5B:
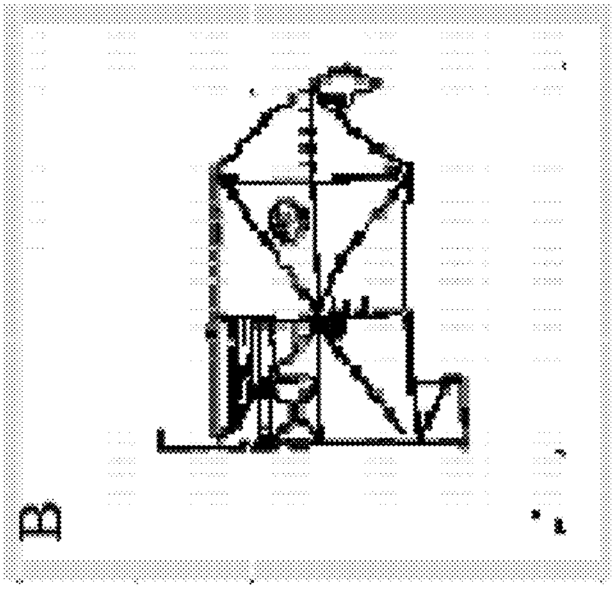
Figure 5A:
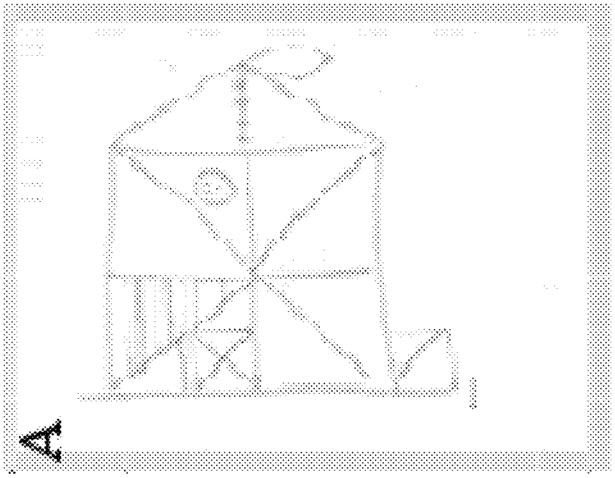

The Delayed Recall drawings were scanned electronically, then rescaled and converted into individual bitmaps (90×124 pixels) using the magick package (FIG. 5B). We also created a control condition by scrambling each image such that the data within each image was relocated to a random index within the image space (FIG. 50).

C. Motor Skill Retention

Figure 6:
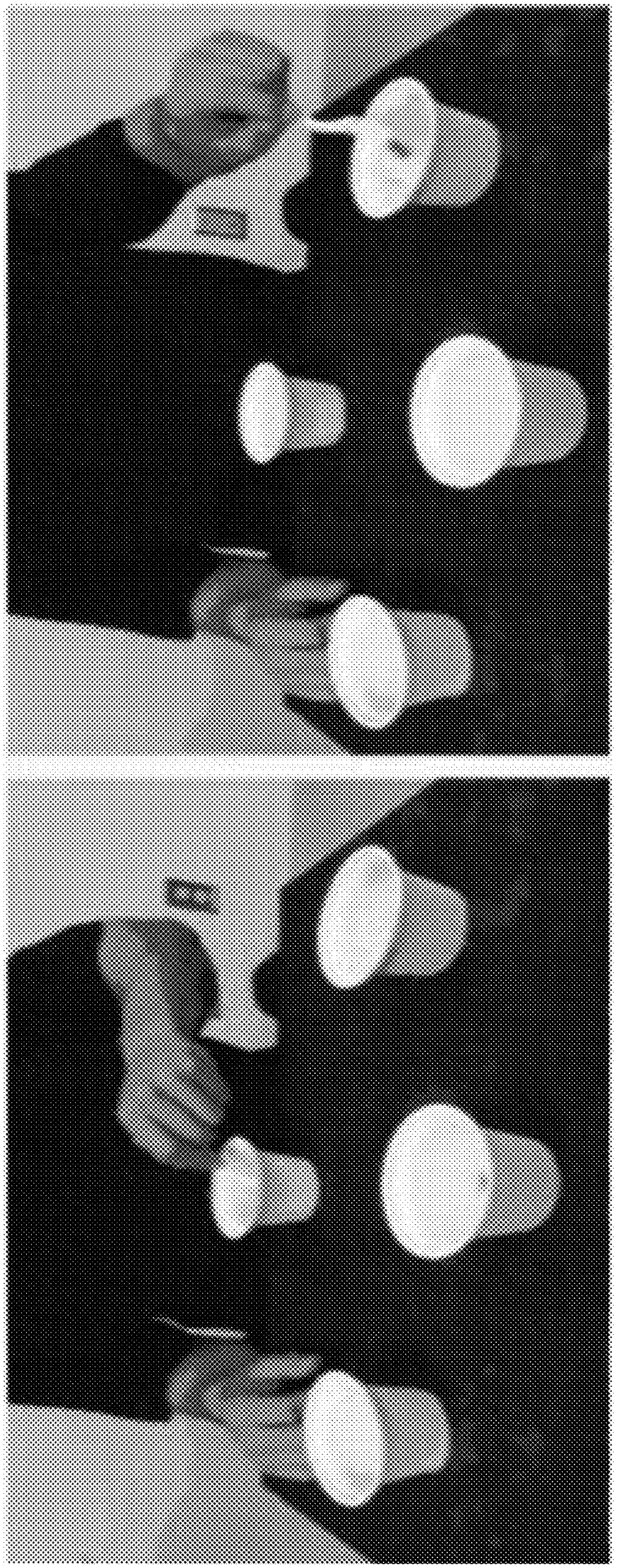
FIG. 6 shows a motor task apparatus, which consisted of a wooden board (43×61 cm) with three different target cups placed radially around a constant 'home' cup at a distance of 16 cm. This image is adapted from the "Dexterity and Reaching Motor Tasks" by MRL Laboratory that is licensed under CC BY 2.0.

Participants completed a baseline trial and three sessions of 50 practice trials of a functional upper-extremity motor task over three consecutive weeks (one session/week). Participants were then re-tested one month after training to evaluate the amount of motor skill retained following a period of no practice. The functional task simulated the basic activity of daily living of feeding oneself (which is often targeted in motor neurorehabilitation) and participants used their nondominant hand to ensure the task was not overlearned (FIG. 6).

Participants were instructed to pick up a standard plastic spoon boated on the ipsilateral side of the home cup and use it to scoop two beans at a time from the home cup to the following sequence of target cups: ipsilateral, middle, then contralateral; this sequence was repeated until the last pair of beans were placed in the contralateral target cup, completing the trial. Participants were timed and instructed to move as quickly and as accurately as possible while freely exploring techniques to enhance performance. Trial time began when the participant picked up the spoon and lower trial times indicated better performance. Since each trial consisted of 15 reaching movements, participants completed 750 reaches per training session, totaling 2,250 across the entire training paradigm. This task has ecological and construct validity, with instructional videos freely available online via the Open Science Framework.

D. Statistical Analysis

Statistical analyses were completed in R (4.0.0). To compare the prediction accuracy of one-month follow-up performance between machine learning models (using pixel image data) and a linear model (using the total image score), we implemented two machine learning approaches: random forest regression and support vector machine regression (SVM). Each model's various hyperparameters (Table 2) were tuned for optimal performance using the mlr library using 10-fold cross validation.

To determine the robustness of each model, we performed 100 iterations of the training and test set validation scheme on each model concurrently, i.e. each model was trained and tested on the same data within each iteration. We chose a 90/10 percent split for training and test sets of the data as pilot work demonstrated this was the optimal split for test set prediction accuracy for each model. We performed the same process using the scrambled data. Rey scores for the linear model were also randomized during the scrambled test phase for consistency across models. We selected mean absolute error (MAE, units are in seconds) as the measure of prediction accuracy of each model so we could easily generalize the accuracy of each model to the motor task. In addition, we calculated the $R^2$, intercept, and slope of each model across all test iterations for both the scrambled and unscrambled datasets. We used a general linear model to compare MAE between (model vs. model) and within image type (scrambled vs. unscrambled) to determine possible improvements in prediction accuracy for each case.

TABLE 2

Hyperparameters for each Machine Learning Model

| Hyperparameter | Random Forest | Support Vector Machine |
|---|---|---|
| Kernel | — | Linear |
| Epsilon | — | 0.39 |
| Cost | — | 9.24 |
| Gamma | — | 4.61 |
| Degree | — | 2 |
| Node Size | 10 | — |
| Max Nodes | 29 | — |
| Number Variables | 3616 | — |
| Number of Trees | 185 | — |

Results

The MAE and regression statistics for the between- and within-model comparisons are provided in Table 3.

TABLE 3

Model Characteristics

| Image Quality | Metric | LM | RF | SVM |
|---|---|---|---|---|
| Unscramble | MAE | 4.91 | 5.1 | 5.45 |
| | $R^2$ | 0.14 | 0.04 | 0.02 |
| | Intercept | 38.6 | 45.8 | 46 |
| | Slope | 0.19 | 0.05 | 0.05 |
| Scramble | MAE | 5.75 | 5.93 | 5.86 |
| | $R^2$ | 0.22 | 0.21 | 0.02 |
| | Intercept | 50.5 | 52 | 49.4 |
| | Slope | −0.05 | −0.09 | −0.02 |

A. Between-Model Comparison

Figure 7:
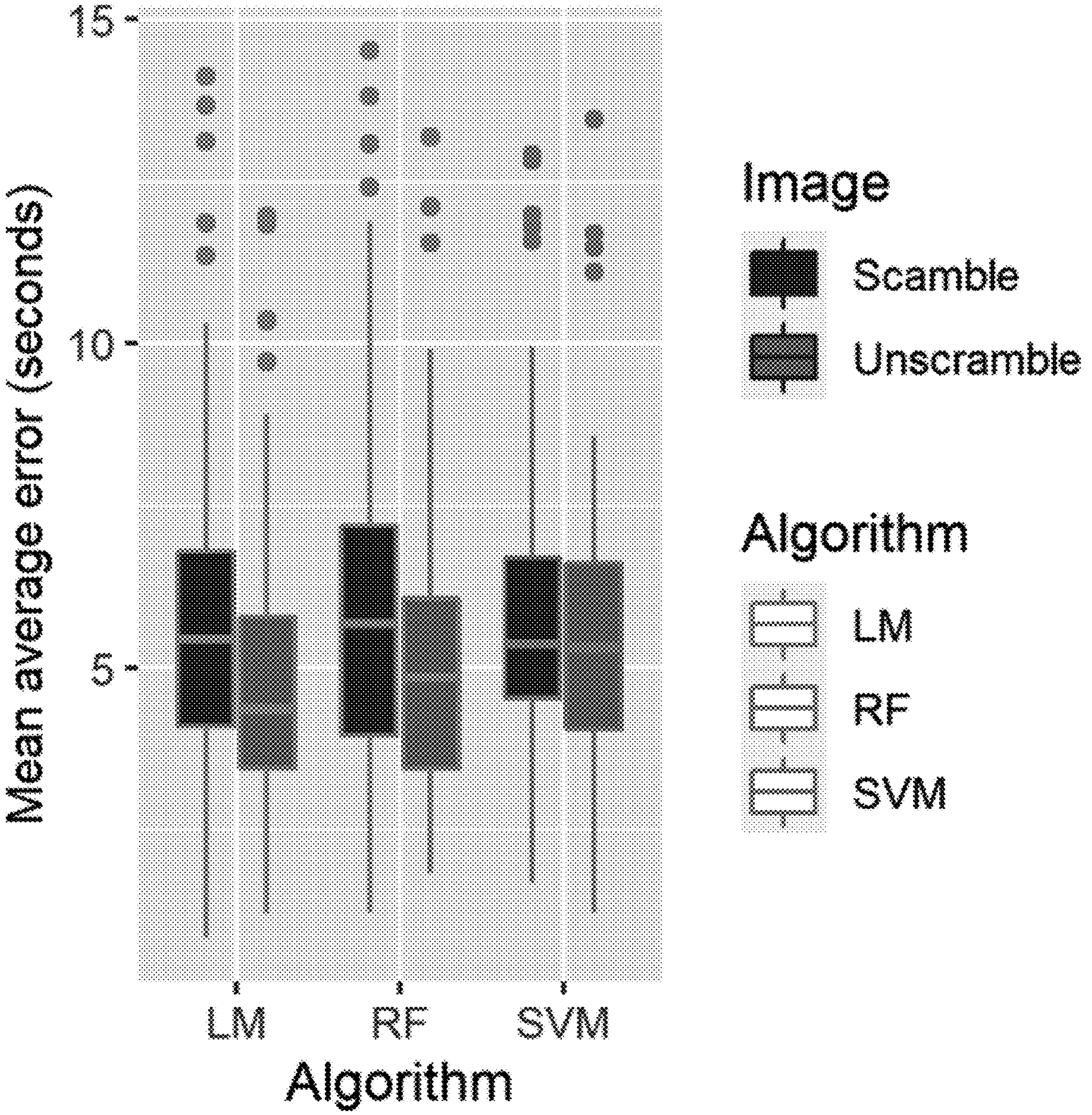
FIG. 7 are boxplots of mean absolute error between models using unscrambled and scrambled images. LM=linear model; RF=random forest; SVM=support vector machine.

Results indicated there was no observable difference between the accuracy of machine learning algorithms that used pixel image data and the linear model that used the Delayed Recall total scores to predict one-month follow-up performance (FIG. 7). The linear and random forest models demonstrated the smallest MAE (4.91 s and 5.1 s, respectively), whereas the SVM model demonstrated the highest error (MAE=5.45 s), although this difference was nonsignificant. These results suggest that machine learning algorithms using pixel data may be capable of equally accurate prediction of one-month follow-up performance (linear and random forest models demonstrated less than 0.2 seconds difference in predictive accuracy) as linear regression that uses manually graded Delayed Recall total scores. Furthermore, this validates this approach to rapidly score this test.

B. Within-Model Comparison

Figure 8B:
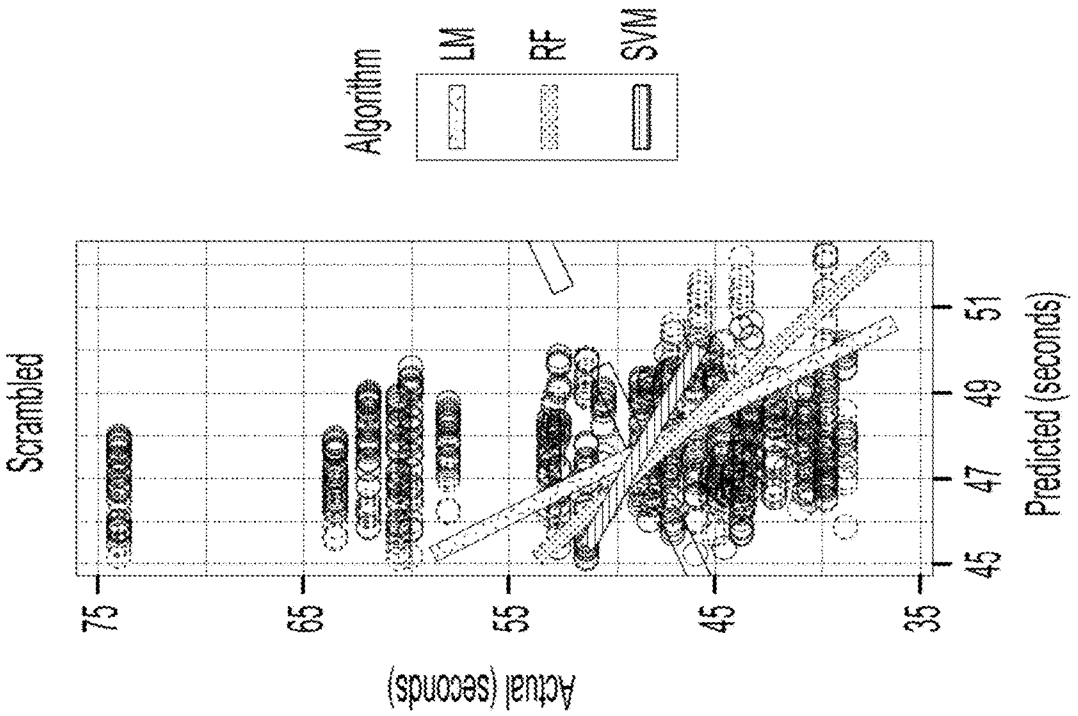
FIGS. 8A-8B are plots showing actual versus predicted one-month motor performance for each model using (A) unscrambled and (B) scrambled images.
Figure 8A:
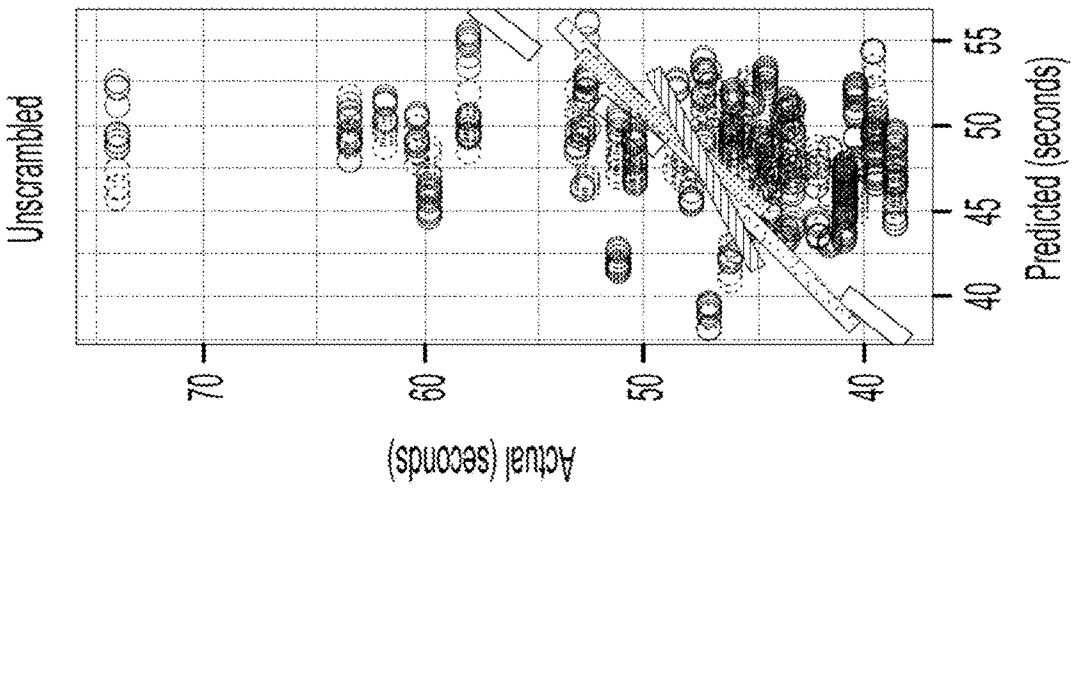

There was a significance difference in prediction accuracy between the models that used unscrambled versus scrambled pixel images, where those using scrambled images yielded greater MAE (difference=−0.6 s, p=0.0002) (FIG. 7). This suggests that the information within the unscrambled image was non-random, and the algorithms identified trends in the images that were predictive of one-month follow-up performance. Visual inspection of the actual versus prediction regression lines of each model demonstrated a stark difference in behavior between each model (for both unscrambled and scrambled conditions) that is not fully captured by the MAE metric (FIG. 8).

C. Variable Importance and Average Support Vector

Figure 9A:
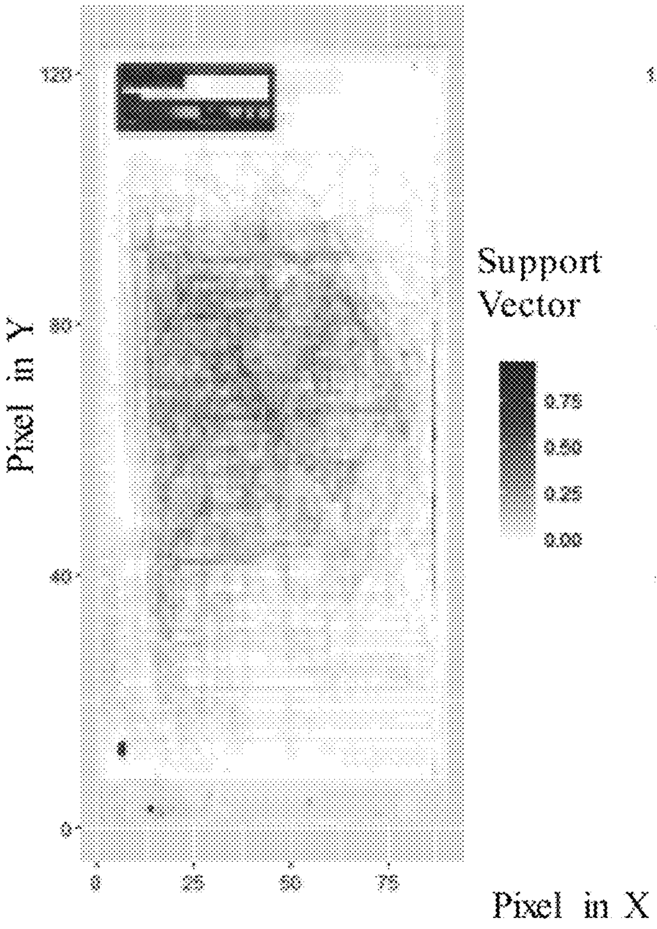
FIGS. 9A-9B are plots showing pixel location data used for calculations made by each respective algorithm (A) support vector and (B) variable importance.
Figure 9B:
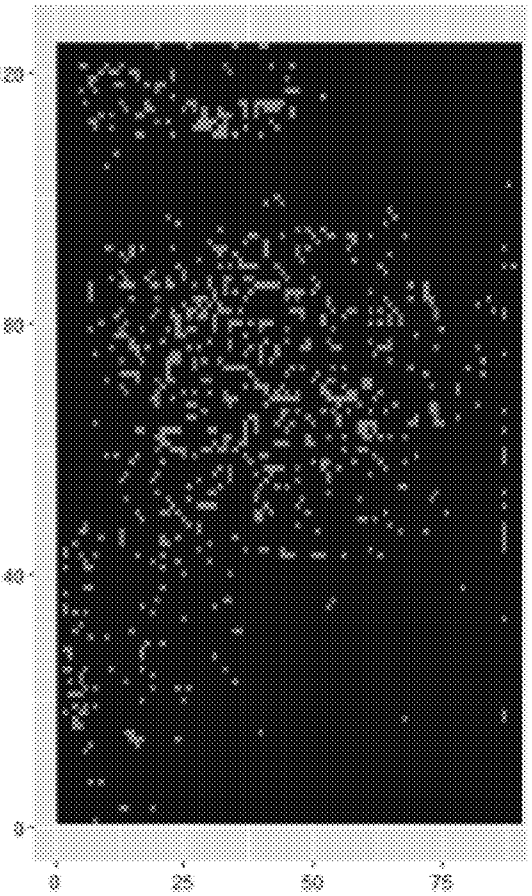

Although random forest and SVM regression are both limited in theft explicit capability of localizing pixels or regions within the image that contributed to accurate prediction, we can identify the area within the image each algorithm drew their calculations, i.e., variable importance and average support vector, respectively. FIG. 9 illustrates that the primary area of prediction for each algorithm rested within the space the participant drew the Delayed Recall image. Thus, each algorithm made predictions from the complex figure drawn by the participant and not randomly from irrelevant regions of the image.

Discussion

Results indicated that the linear model demonstrated highest prediction accuracy, although the linear and machine learning approaches yielded comparable results. One potentially exciting implication from this work is the utility of machine learning-based applications in predicting rehabilitation responsiveness using patient-generated data (i.e., drawing). As this test can be administered via teletherapy and does not involve manually scoring, both clinicians and researchers could benefit from its application.

As these machine learning algorithms did not assign a high or low score (associated with high or low visuospatial memory), they made no assumptions based on which sections of the image are missing and/or errors present in the drawings; rather, each algorithm simply drew comparisons across all pixels from each image and identified a relationship with motor behavior. Several questions emerge that future studies will address: Considering the algorithms used unscored images to draw connections between pixel location(s) and motor behavior, are features within the pixel data more sensitive to motor performance than the Delayed Recall scoring rubric? Moreover, can features within the pixel data also predict future cognitive decline or onset of neurodegenerative disease (e.g., Alzheimer's disease)? A recent study reported that cognitive measures may predict the onset of mild cognitive impairment 20 years prior diagnosis; whether our algorithms would yield comparable results remains unexplored.

We acknowledge the small sample size as a limitation, which restricted our analyses to a conservative training/test split. However, iteratively performing the training/test protocols many times over allows us to better generalize our findings. As the dataset increases, we anticipate the algorithms will improve prediction accuracy. With a larger dataset of Delayed Recall images and motor performance scores, it may be plausible for the algorithms to surpass that of the graded scores as they identified relationships made from pixel-comparison and not from interpretation of Delayed Recall errors. Future work will involve expanding the dataset and extending this approach into neuropathological populations to further understand how these algorithms may provide refined prediction based on an individual's cognition or diagnosis.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, systems, and/or computer readable media or other aspects thereof can be used in various combinations. All patents, patent applications, websites, other publications or documents, and the like cited herein are incorporated by reference in their entirety for all purposes to the same extent as if each individual item were specifically and individually indicated to be so incorporated by reference.

What is claimed is:

1. A method of providing personalized patient treatment to a test subject, the method comprising:

receiving, by a computer from a digital imaging device, a set of images of a hand-drawn rendition of a target image produced by the test subject as drawn by the test subject, the hand-drawn rendition comprising a Rey-Osterrieth Complex Figure, wherein at least a first of the images comprises a rendition of the target image produced by the test subject at a first time point, and wherein at least a second of the images comprises a rendition of the target image produced by the test subject at a second time point that differs from the first time point to produce test subject data;

passing, by the computer, the test subject data through a machine learning algorithm configured to extract spatial and temporal drawing features directly from the digital images without prior image segmentation, wherein the machine learning algorithm comprises an electronic neural network trained end-to-end on whole-figure images, wherein the machine learning algorithm has been trained on a set of training data that comprises a plurality of reference subject data sets that are each labeled with at least a neuropsychological functioning score of a given reference subject data set in the plurality of reference subject data sets, wherein the plurality of reference subject data sets comprises sets of images produced by reference subjects, and wherein at least a first and a second of the images in a given set comprises renditions of the target image produced by a given reference subject at different time points;

outputting, by the computer, from the machine learning algorithm at least a neuropsychological functioning score indicated by the test subject data, wherein the machine learning algorithm is robust to variations in size and position among the hand-drawn renditions such that image segmentation or editing is not required for accurate score prediction, wherein the neuropsychological functioning score is predicted directly from pixel-level input without manual feature extraction, wherein a correlation value between the neuropsychological functioning score and a human graded score generated for the set of images is at least about 0.8, and wherein a time taken to perform the receiving, passing, and outputting steps comprises less than about 3.0 seconds per image in the set of images; and, automatically initiating, by the computer, ordering one or more medical tests for, and/or administering or discontinuing administering one or more therapies to, the test subject when the neuropsychological functioning score indicated by the test subject data varies from a predetermined threshold value, thereby providing the personalized patient treatment to the test subject.

2. The method of claim 1, wherein the set of training data comprises at least about 10 reference subject data sets, at least about 100 reference subject data sets, at least about 1,000 reference subject data sets, at least about 10,000 reference subject data sets, at least about 100,000 reference subject data sets, at least about 1,000,000 reference subject data sets, at least about 10,000,000 reference subject data sets, at least about 100,000,000 reference subject data sets, or more reference subject data sets.

3. The method of claim 1, comprising vectorizing the set of images produced by the test subject.

4. The method of claim 1, wherein the neuropsychological functioning score comprises one or more of a visuospatial recall memory score, a visuospatial recognition memory score, a response bias score, a processing speed score, and a visuospatial constructional ability score.

5. The method of claim 1, further comprising generating a medical report for the test subject when the neuropsychological functioning score indicated by the test subject data varies from the predetermined threshold value.

6. The method of claim 1, wherein the machine learning algorithm comprises a support vector machine regression (SVMr) algorithm.

7. The method of claim 1, wherein the electronic neural network comprises at least one layer that performs a regression operation to generate the neuropsychological functioning score.

8. A system for providing personalized patient treatment to a test subject, the system comprising:

a processor; and a memory communicatively coupled to the processor, the memory storing instructions which, when executed on the processor, perform operations comprising:

receiving from a digital imaging device a set of images of a hand-drawn rendition of a target image produced by the test subject as drawn by the test subject, the hand-drawn rendition comprising a Rey-Osterrieth Complex Figure, wherein at least a first of the images comprises a rendition of the target image produced by the test subject at a first time point, and wherein at least a second of the images comprises a rendition of the target image produced by the test subject at a second time point that differs from the first time point to produce test subject data;

passing test subject data for the test subject through a machine learning algorithm configured to extract spatial and temporal drawing features directly from the digital images without prior image segmentation, wherein the machine learning algorithm comprises an electronic neural network trained end-to-end on whole-figure images, wherein the machine learning algorithm has been trained on a set of training data that comprises a plurality of reference subject data sets that are each labeled with at least a neuropsychological functioning score of a given reference subject data set in the plurality of reference subject data sets, wherein the plurality of reference subject data sets comprises sets of images produced by reference subjects, and wherein at least a first and a second of the images in a given set comprises renditions of the target image produced by a given reference subject at different time points;

outputting from the machine learning algorithm at least a neuropsychological functioning score indicated by the test subject data, wherein the machine learning algorithm is robust to variations in size and position among the hand-drawn renditions such that image segmentation or editing is not required for accurate score prediction, wherein the neuropsychological functioning score is predicted directly from pixel-level input without manual feature extraction, wherein a correlation value between the neuropsychological functioning score and a human graded score generated for the set of images is at least about 0.8, and wherein a time taken to perform the receiving, passing, and outputting steps comprises less than about 3.0 seconds per image in the set of images; and, automatically initiating ordering one or more medical tests for, and/or recommending administering or discontinuing administering one or more therapies to, the test subject when the neuropsychological functioning score indicated by the test subject data varies from a predetermined threshold value.

9. The system of claim 8, wherein the neuropsychological functioning score comprises one or more of a visuospatial recall memory score, a visuospatial recognition memory score, a response bias score, a processing speed score, and a visuospatial constructional ability score.

10. The system of claim 8, wherein the system generates a medical report for the test subject when the neuropsychological functioning score indicated by the test subject data varies from the predetermined threshold value.

11. The system of claim 8, wherein the machine learning algorithm comprises a support vector machine regression (SVMr) algorithm.

12. The system of claim 8, wherein the machine learning algorithm comprises an electronic neural network.

13. A non-transitory computer readable media for providing personalized patient treatment to a test subject, the non-transitory computer readable media comprising computer executable instruction which, when executed by at least electronic processor, perform at least:

receiving from a digital imaging device a set of images of a hand-drawn rendition of a target image produced by the test subject as drawn by the test subject, the hand-drawn rendition comprising a Rey-Osterrieth Complex Figure, wherein at least a first of the images comprises a rendition of the target image produced by the test subject at a first time point, and wherein at least a second of the images comprises a rendition of the target image produced by the test subject at a second time point that differs from the first time point to produce test subject data;

passing test subject data for the test subject through a machine learning algorithm configured to extract spatial and temporal drawing features directly from the digital images without prior image segmentation, wherein the machine learning algorithm comprises an electronic neural network trained end-to-end on whole-figure images, wherein the machine learning algorithm has been trained on a set of training data that comprises a plurality of reference subject data sets that are each labeled with at least a neuropsychological functioning score of a given reference subject data set in the plurality of reference subject data sets, wherein the plurality of reference subject data sets comprises sets of images produced by reference subjects, and wherein at least a first and a second of the images in a given set comprises renditions of the target image produced by a given reference subject at different time points;

outputting from the machine learning algorithm at least a neuropsychological functioning score indicated by the test subject data, wherein the machine learning algorithm is robust to variations in size and position among the hand-drawn renditions such that image segmentation or editing is not required for accurate score prediction, wherein the neuropsychological functioning score is predicted directly from pixel-level input without manual feature extraction, wherein a correlation value between the neuropsychological functioning score and a human graded score generated for the set of images is at least about 0.8, and wherein a time taken to perform the receiving, passing, and outputting steps comprises less than about 3.0 seconds per image in the set of images; and, automatically initiating ordering one or more medical tests for, and/or recommending administering or discontinuing administering one or more therapies to, the test subject when the neuropsychological functioning score indicated by the test subject data varies from a predetermined threshold value.

* * * * *